(12) United States Patent
O'Brien et al.

(10) Patent No.: US 7,879,942 B2
(45) Date of Patent: Feb. 1, 2011

(54) SWITCHABLE ADHESIVE ARTICLE FOR ATTACHMENT TO SKIN AND METHOD OF USING THE SAME

(75) Inventors: Emmett Patrick O'Brien, Johnson City, TN (US); Douglas Grant Atkins, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 795 days.

(21) Appl. No.: 11/543,620

(22) Filed: Oct. 5, 2006

(65) Prior Publication Data

US 2008/0085972 A1 Apr. 10, 2008

(51) Int. Cl.
*C08G 18/42* (2006.01)
(52) U.S. Cl. ........................ 524/500; 428/480
(58) Field of Classification Search ................ 524/500; 428/480

See application file for complete search history.

(56) References Cited

U.S. PATENT DOCUMENTS

| | | | |
|---|---|---|---|
| 2,727,846 A | 12/1955 | Talbot | |
| 2,804,073 A | 8/1957 | Gallienne et al. | |
| 3,577,516 A | 5/1971 | Gould et al. | |
| 3,608,070 A | 9/1971 | Nouvel | |
| 3,655,129 A | 4/1972 | Seiner | |
| 3,685,734 A | 8/1972 | Paciorek et al. | |
| 3,731,683 A | 5/1973 | Zaffaroni | |
| 3,734,874 A | 5/1973 | Kibler et al. | |
| 3,779,993 A | 12/1973 | Kibler et al. | |
| 3,803,300 A | 4/1974 | Pospischil | |
| 3,828,010 A | 8/1974 | Davis et al. | |
| 4,011,388 A | 3/1977 | Murphy et al. | |
| 4,052,368 A | 10/1977 | Larson | |
| 4,233,196 A | 11/1980 | Sublett | |
| 4,304,901 A | 12/1981 | O'Neill et al. | |
| 4,335,220 A | 6/1982 | Coney | |
| 4,355,046 A | 10/1982 | Suess | |
| 4,413,073 A | 11/1983 | Gibson et al. | |
| 4,451,596 A | 5/1984 | Wilk et al. | |
| 4,540,749 A | 9/1985 | Meyer, Jr. et al. | |
| 4,542,012 A | 9/1985 | Dell | |
| 4,604,446 A | 8/1986 | Sand et al. | |
| 4,665,153 A | 5/1987 | Beavers et al. | |
| 4,784,857 A | 11/1988 | Berry et al. | |
| 4,834,979 A | 5/1989 | Gale | |
| 4,946,932 A | 8/1990 | Jenkins | |
| 4,950,475 A | 8/1990 | Vishnupad et al. | |
| 4,977,191 A | 12/1990 | Salsman | |
| 4,990,593 A | 2/1991 | Blount | |
| 4,992,508 A | 2/1991 | Vishnupad et al. | |
| 4,994,267 A | 2/1991 | Sablotsky | |
| 4,994,278 A | 2/1991 | Sablotsky et al. | |
| 5,006,598 A | 4/1991 | Adams et al. | |
| 5,021,257 A | 6/1991 | Foster et al. | |
| 5,032,637 A | 7/1991 | Therriault et al. | |
| 5,098,962 A | 3/1992 | Bozich | |
| 5,156,911 A | 10/1992 | Stewart | |
| 5,218,042 A | 6/1993 | Kuo et al. | |
| 5,225,473 A | 7/1993 | Duan | |
| 5,266,322 A | 11/1993 | Myers et al. | |
| 5,270,111 A | 12/1993 | D'Haese et al. | |
| 5,274,025 A | 12/1993 | Stockl et al. | |
| 5,281,630 A | 1/1994 | Salsman | |
| 5,300,299 A | 4/1994 | Sweet et al. | |
| 5,322,885 A | 6/1994 | Kuo | |
| 5,411,737 A | 5/1995 | Hsu et al. | |
| 5,422,397 A | 6/1995 | Brekner et al. | |
| 5,500,265 A | 3/1996 | Ambroise et al. | |
| 5,503,844 A | 4/1996 | Kwiatek et al. | |
| 5,505,958 A | 4/1996 | Bello et al. | |
| 5,534,247 A | 7/1996 | Franjac et al. | |
| 5,538,760 A | 7/1996 | Sharma | |
| 5,543,488 A | 8/1996 | Miller et al. | |
| 5,552,495 A | 9/1996 | Miller et al. | |
| 5,552,511 A | 9/1996 | Miller et al. | |
| 5,559,192 A | 9/1996 | Bors et al. | |
| 5,562,917 A | 10/1996 | Durif et al. | |
| 5,569,715 A | 10/1996 | Grandhee | |

(Continued)

FOREIGN PATENT DOCUMENTS

DE 3 811 564 10/1989

(Continued)

OTHER PUBLICATIONS

PCT International Search Report and Written Opinion for PCT/US2007/020063 dated Sep. 14, 2007.

(Continued)

*Primary Examiner*—Edward J Cain
(74) *Attorney, Agent, or Firm*—Polly C. Owen; Bernard J. Graves, Jr.

(57) ABSTRACT

A hypoallergenic adhesive article employing a switchable pressure sensitive adhesive (PSA) composition comprising one or more amphiphilic polyesters in physical mixture with a humectant. When contacted with a liquid of low-ion content, the adhesive undergoes a reduction in peel strength, which allows for easy removal, but remains strongly adhered when contacted with ionic liquids, such as blood, sweat, and other bodily fluids. The adhesive composition can be employed in a variety of medical articles or in other similar applications.

17 Claims, No Drawings

U.S. PATENT DOCUMENTS

| | | |
|---|---|---|
| 5,571,876 A | 11/1996 | Miller et al. |
| 5,605,764 A | 2/1997 | Miller et al. |
| 5,626,866 A | 5/1997 | Ebert et al. |
| 5,686,518 A | 11/1997 | Fontenot et al. |
| 5,702,721 A | 12/1997 | Horstmann et al. |
| 5,709,940 A | 1/1998 | George et al. |
| 5,726,277 A | 3/1998 | Salsman |
| 5,744,538 A | 4/1998 | Miller et al. |
| 5,750,605 A | 5/1998 | Blumenthal et al. |
| 5,780,047 A | 7/1998 | Kamiya et al. |
| 5,780,050 A | 7/1998 | Jain et al. |
| 5,780,151 A | 7/1998 | Miller et al. |
| 5,843,468 A | 12/1998 | Burkoth et al. |
| 5,874,164 A | 2/1999 | Caldwell |
| 5,925,364 A | 7/1999 | Ribier et al. |
| 5,928,460 A | 7/1999 | Miller et al. |
| 5,939,085 A | 8/1999 | Jacobs et al. |
| 5,948,400 A | 9/1999 | Brett |
| 5,962,011 A | 10/1999 | DeVillez et al. |
| 5,965,154 A | 10/1999 | Haralambopoulos |
| 6,001,910 A | 12/1999 | Blumenthal et al. |
| 6,001,922 A | 12/1999 | Clark et al. |
| 6,007,749 A | 12/1999 | Wang et al. |
| 6,007,910 A | 12/1999 | Miller et al. |
| 6,010,686 A | 1/2000 | De La Poterie et al. |
| 6,010,716 A | 1/2000 | Saunal et al. |
| 6,034,168 A | 3/2000 | Wang |
| 6,036,962 A | 3/2000 | Müller et al. |
| 6,113,981 A | 9/2000 | Ogilvie, Jr. et al. |
| 6,126,948 A | 10/2000 | Simonnet et al. |
| 6,139,827 A | 10/2000 | Cohen et al. |
| 6,143,319 A | 11/2000 | Meconi et al. |
| 6,162,890 A | 12/2000 | George et al. |
| 6,190,689 B1 | 2/2001 | Hoffmann et al. |
| 6,211,282 B1 | 4/2001 | Mantelle et al. |
| 6,232,366 B1 | 5/2001 | Wang et al. |
| 6,329,485 B1 | 12/2001 | Vanderbilt |
| 6,333,053 B1 | 12/2001 | Simon |
| 6,368,687 B1 | 4/2002 | Joseph et al. |
| 6,428,900 B1 | 8/2002 | Wang |
| 6,491,929 B1 | 12/2002 | Anderson |
| 6,555,730 B1 | 4/2003 | Albrod et al. |
| 6,562,363 B1 | 5/2003 | Mantelle et al. |
| 6,572,600 B1 | 6/2003 | Roe et al. |
| 6,582,683 B2 | 6/2003 | Jezior |
| 6,620,890 B1 | 9/2003 | Yamashita et al. |
| 6,627,309 B2 | 9/2003 | Stebbings et al. |
| 6,645,609 B2 | 11/2003 | Sperlich et al. |
| 6,664,309 B2 | 12/2003 | Svenningsen et al. |
| 6,685,682 B1 | 2/2004 | Heinecke et al. |
| 6,746,779 B2 | 6/2004 | Hayes et al. |
| 6,749,948 B2 | 6/2004 | Sperlich et al. |
| 6,756,059 B2 | 6/2004 | Roszell et al. |
| 6,770,361 B2 | 8/2004 | Kong |
| 6,803,420 B2 | 10/2004 | Cleary et al. |
| 6,822,012 B1 | 11/2004 | Baumgart et al. |
| 6,841,716 B1 | 1/2005 | Tsutsumi |
| 6,860,961 B2 | 3/2005 | Gibes et al. |
| 6,967,261 B1 | 11/2005 | Soerens et al. |
| 6,998,432 B2 | 2/2006 | Murakami et al. |
| 7,049,479 B2 | 5/2006 | Cleary et al. |
| 2002/0077377 A1 | 6/2002 | Zhang et al. |
| 2002/0115744 A1 | 8/2002 | Svenningsen et al. |
| 2002/0131994 A1 | 9/2002 | Schur et al. |
| 2003/0095941 A1 | 5/2003 | Anderson |
| 2003/0147829 A1 | 8/2003 | Oldfield et al. |
| 2003/0152612 A1 | 8/2003 | Pugliese et al. |
| 2003/0157138 A1 | 8/2003 | Eini et al. |
| 2003/0175333 A1 | 9/2003 | Shefer et al. |
| 2003/0176467 A1 | 9/2003 | Andersson et al. |
| 2003/0185774 A1 | 10/2003 | Dobbs et al. |
| 2003/0224053 A1 | 12/2003 | Fotinos et al. |
| 2003/0228337 A1 | 12/2003 | Faryniarz et al. |
| 2004/0028727 A1 | 2/2004 | Glenn et al. |
| 2004/0033254 A1 | 2/2004 | Song et al. |
| 2004/0115458 A1 | 6/2004 | Kong |
| 2004/0127531 A1 | 7/2004 | Lu et al. |
| 2004/0136937 A1 | 7/2004 | Cassin |
| 2004/0142024 A1 | 7/2004 | Chono et al. |
| 2004/0161402 A1 | 8/2004 | Brooks |
| 2004/0202859 A1 | 10/2004 | Sheu |
| 2004/0224007 A1 | 11/2004 | Zhang |
| 2004/0258910 A1 | 12/2004 | Haile et al. |
| 2005/0008802 A1 | 1/2005 | Malfait et al. |
| 2005/0019291 A1 | 1/2005 | Zolotarsky et al. |
| 2005/0042271 A1 | 2/2005 | Xiong et al. |
| 2005/0095279 A1 | 5/2005 | Gale et al. |
| 2005/0175560 A9 | 8/2005 | Ferrari |
| 2005/0182443 A1 | 8/2005 | Jonn et al. |
| 2005/0233149 A1 | 10/2005 | Ansell |
| 2005/0282008 A1 | 12/2005 | Haile et al. |
| 2006/0024259 A1 | 2/2006 | Vrignaud et al. |
| 2006/0045857 A1 | 3/2006 | Roszell |
| 2006/0246021 A1 | 11/2006 | Roszell |
| 2007/0259029 A1* | 11/2007 | McEntire et al. ............ 424/449 |

FOREIGN PATENT DOCUMENTS

| | | |
|---|---|---|
| EP | 0 750 905 A2 | 1/1997 |
| EP | 0 861 655 A2 | 9/1998 |
| EP | 1 704 849 A1 | 9/2006 |
| JP | 62 016185 | 1/1987 |
| JP | 1996175979 A | 7/1996 |
| JP | 1996319453 A | 12/1996 |
| JP | 1997099050 A | 4/1997 |
| JP | 200263716 A | 9/2000 |
| JP | 2003089169 A | 3/2003 |
| WO | 97/24102 A1 | 7/1997 |
| WO | 00/16752 A2 | 3/2000 |
| WO | 00/24371 A1 | 5/2000 |
| WO | 00/30578 A1 | 6/2000 |
| WO | 00/51553 A1 | 9/2000 |
| WO | 01/66666 A2 | 9/2001 |
| WO | WO 01/66666 A2 | 9/2001 |
| WO | 2004/113598 A2 | 12/2004 |
| WO | 2005/074894 A1 | 8/2005 |
| ZA | 97/5168 | 11/1996 |

OTHER PUBLICATIONS

Robin A. Chivers, International Journal of Adhesion & Adhesives 21 (2001), pp. 381-388; Easy Removal of Pressure Sensitive Adhesives for Skin Applications; Mar. 16, 2006.
Mitchell L. Schlossman, B.A., FAIC, FSCC, The Chemistry and Manufacture of Cosmetics vol. III—Ingredients, Third Edition, pp. 469-489, 2002.
I. Webster, International Journal of Adhesion & Adhesives, The Development of a Pressure-Sensitive Adhesive for Trauma-Free Removal, 19, pp. 29-34, 1999.
Boyne et al, International Journal of Adhesion & Adhesives, Peeling Performance of a Novel Light Switchable Pressure-Sensitive Adhesive, 21, pp. 49-53, 2001.
Trenor et al, The Journal of Adhesion, Development of a Light-Deactivatable PSA Via Photodimerization, 81, pp. 213-229, 2005.
Mayrovitz et al, Advances in Wound Care, Laser-Doppler Imaging Assessment of Skin Hyperemia as an Indicator of Trauma After Adhesive Strip Removal, 9, pp. 38-42, 1996.
Clarke et al, Adhesives Age, Temperature Switchable Pressure Sensitive Adhesives, pp. 39-41, 1993.
Schiraldi, TAPPI Proceedings, Polymers, Laminations & Coatings Conference, Book 1, pp. 63-70, 1990.
ASTM D882, pp. 167-176. (Jun. 2002).
ASTM D3835-79, p. 216-226. (Jan. 2003).
D-247 ON Oil-acrylic Hybrid Emulsions 9EMS van Hamersveld, Eidenhoven, pp. 247-257. (Aug. 1999).

British Journal of Dermatology, p. 63-68, Jan. 1985.
The Journal of Investigative Dermatology, p. 152-155, Mar. 1978.
The International Journal of Clinical Practice, p. 9-14, p. 23, Feb. 2003.
McCutcheon's Emulsifiers and Detergents, North American Edition, MC Publishing Co, Glen Rock, NJ, pp. 1-224, 1997.
Lowe, N.J, Shaath, N.A., Editors; "Sunscreens, Development, Evaluation and Regulatory Aspects"; Marcel Dekker, Inc., 1990, Chapter 1.
Title: Oxytrol URL: http://www.fda.gov/eder/foi/label/2003/21351_oxytrol_lbl.pdf.
U.S. Appl. No. 60/798,574 filed May 8, 2006, Rebecca Reid Stockl, et al.
U.S. Appl. No. 60/798,575 filed May 8, 2006, Rebecca Reid Stockl, et al.
U.S. Appl. No. 11/800,722 filed May 7, 2008, Edward Enns McEntire, et al.
U.S. Appl. No. 11/800,727 filed May 7, 2008, Edward Enns McEntire, et al.
U.S. Appl. No. 11/515,150 filed Sep. 1, 2006, Edward Enns McEntire, et al.
Notification of Transmittal of the International Search Report and the Written Opinion of the International Searching Authority or the Declaration, PCT/US2007/011035, International Filing Date: May 8, 2007.
Notification of Transmittal of the International Search Report and the Written Opinion of the International Searching Authority, or the Declaration, PCT/US2007/011036, International Filing Date: May 8, 2007.
Office Action date of mailing Jul. 20, 009 received in co-pending U.S. Appl. No. 11/800,727.
Polymer Gels and Networks 1 (1993) p. 5-17.
Office Action date of mailing Sep. 14, 2009 received in co-pending U.S. Appl. No. 11/515,150.
Office Action date of mailing Apr. 14, 2010 received in co-pending U.S. Appl. No. 11/800,727.
Office Action date of mailing Apr. 26, 2010 received in co-pending U.S. Appl. No. 11/800,722.

* cited by examiner

SWITCHABLE ADHESIVE ARTICLE FOR ATTACHMENT TO SKIN AND METHOD OF USING THE SAME

BACKGROUND OF THE INVENTION

1. Field of the Invention

This invention generally relates to an adhesive article employing a switchable pressure sensitive adhesive (PSA) that is suitable for attachment to the skin and a method for using the same. In another aspect, the invention concerns a water-dispersible PSA composition comprising a physical mixture of one or more amphiphilic polyesters and a humectant.

2. Description of the Prior Art

Pressure-sensitive adhesives are used in a variety of industrial, consumer, and medical applications. Medical-use PSA are applied to a variety of backings for use as occlusive or non-occlusive adhesive articles such as bandages, wound dressings, analgesic or transdermal drug delivery patches, monitoring sensors, stimulating electrodes, and the like. Desirably, the properties of the PSA allow the medical article to remain adhered to a wearer's skin despite changing conditions, such as movement or perspiration. Additionally, the article should be removable in a way that avoids irritating the wearer's skin. Minimizing skin damage upon removal is especially important in the case of a PSA article applied to sensitive areas or in situations wherein repeat article application is required.

The objectives of improving the tack of a PSA while reducing skin irritation caused by the removal of the PSA article seemingly conflict because generally, superior adhesion increases the risk of intensifying removal trauma. One proposed solution is to utilize adhesive compositions that include latex and/or acrylic. Not only do articles employing these adhesives fail to minimize skin damage during removal, but the use of latex and/or acrylic polymers precludes the use of these articles by people with latex and/or acrylic skin allergies. Another proposed solution is to use medical articles employing a PSA that is "deactivated" by contact with a chemical or through temperature change or exposure to radiation. Typically, however, the deactivation chemical is a harsh, skin-irritating solvent and exposure to heat, cold, and/or radiation is often inconvenient and/or not suitable for the affected area.

Thus, a need exists for a robust, medical-use pressure sensitive adhesive article that can be conveniently removed in a way that avoids irritating the wearer's skin.

SUMMARY OF THE INVENTION

In one embodiment of the present invention, there is provided a pressure sensitive adhesive (PSA) suitable for attachment to skin. The PSA comprises one or more water-dispersible sulfonated polyesters and a humectant in physical mixture with the polyesters. The PSA has a pH in the range of from about 6 to about 8.5.

In another embodiment of the present invention, there is provided a pressure sensitive adhesive (PSA) comprising one or more amphiphilic water-dispersible polyesters, a humectant, and, optionally, a cold flow reducing agent having a molecular weight less than 1,500 grams per mole. The PSA contains greater than 80 weight percent of the amphiphilic water-dispersible polyester(s) and in the range of from about 0 to about 4 weight percent of the cold flow reducing agent. The PSA has an average wet standard peel strength that is less than about 75 percent of the average dry standard peel strength of the PSA, a loop tack in the range of from about 0.1 to about 10 pound-force per inch (lbf/in), a glass transition temperature (Tg) in the range of from about −10 to about 15° C., and a moisture mass uptake greater than about 6 weight percent.

In a further embodiment of the present invention, there is provided a switchable adhesive article suitable for attachment to the skin. The article comprises a backing and a pressure sensitive adhesive (PSA) applied to the backing. The PSA comprises one or more water-dispersible sulfonated polyesters in physical mixture with a humectant. The PSA has a pH in the range of from about 6 to about 8.5.

In yet another embodiment of the present invention, there is provided a method of attaching and removing a switchable adhesive article to and from skin. The method comprises: (a) adhering a switchable adhesive article to skin, wherein the adhesive article comprises a backing and a pressure sensitive adhesive (PSA) applied to a first side of the backing, and wherein the PSA comprises at least one sulfonated water-dispersible polyester; (b) applying a low-ion liquid to the PSA; and (c) subsequent to step (b), removing the article from the skin, wherein the average skin peel strength of the PSA subsequent to step (b) is less than about 75 percent of the average skin peel strength of the PSA prior to step (b).

DETAILED DESCRIPTION

The present invention provides a pressure sensitive adhesive article that employs a novel PSA blend. The inventive adhesive composition undergoes a substantial reduction in peel strength upon contact with a non-irritating, low-ion content liquid (e.g., water). This "switchable" PSA, however, remains firmly adhered to a substrate (e.g., skin) when exposed to ionic liquids, such as blood, sweat, and the like. Along with its hypoallergenic formulation, this makes the PSA of the present invention particularly suitable for attachment to skin and for use in medical articles such as, for example, wound and surgical dressings, athletic or medical tapes, non-occlusive patches for transdermal drug delivery, and tapes or tabs for attaching medical devices such as electrodes or sensors, and the like.

The PSA of the present invention comprises one or more amphiphilic polyesters in physical mixture with a humectant. The amphiphilic nature of the polyesters contributes to the ability of the adhesive to be dispersible in low-ion liquids. In one embodiment, the low-ion liquid can comprise water and the amphiphilic polyesters can be water-dispersible. In another embodiment, the amphiphilic polyesters can be water-dispersible sulfonated polyesters, as disclosed in U.S. Pat. Nos. 5,552,495 and 5,543,488, both of which are incorporated herein by reference.

In accordance with one embodiment, the adhesive can comprise a blend of at least one linear and/or at least one branched sulfonated polyester. In one embodiment, the linear water-dispersible sulfonated polyester condensation polymer comprises the reaction product of:
  (i) at least one difunctional dicarboxylic acid which is not a sulfomonomer;
  (ii) about 4 to 25 mole percent, based on the total of all acid, hydroxyl and amino equivalence, of residues of at least one difunctional sulfomonomer containing at least one sulfonate group bonded to an aromatic ring wherein the functional groups are hydroxyl, carboxyl, or amino;
  (iii) at least one diol or a mixture of a diol and a diamine comprising:
    (A) at least 15 mole percent, based on the total mole percent of diol moieties or diol and diamine moieties, of a diol or diamine having the formula H(—OCH$_2$CH$_2$—)$_n$OH and HRN(—OH$_2$CH$_2$O—)$_n$ NRH wherein n is 2 to about 20 and R is hydrogen or C$_1$-C$_6$ alkyl, (B) about 0.1 to less than about 15 mole percent, based on the total mole percent of diol moieties or diol and diamine moieties, of moieties of a poly(ethylene glycol) having the formula H(—OCH$_2$ CH$_2$—)$_n$ OH wherein n is 2 to about 500, provided that the mole percent of such moieties is inversely proportional to the value of n; and, (iv) 0 to about 40 mole percent moieties of a difunctional monomer reactant selected from hydroxycarboxylic acids, amino-carboxylic acids and aminoalkanols; the polymer containing substantially equal mole proportions of acid equivalents (100 mole percent) and diol or diol and diamine equivalents (100 mole percent).

According to another embodiment, the branched water-dispersible sulfonated polyester condensation polymer comprises the reaction product of:

(a) at least one difunctional dicarboxylic acid which is not a sulfomonomer;

(b) about one to 20 mole percent, based on the total of acid, hydroxyl and amino equivalents, of residues of at least one difunctional sulfomonomer containing at least one sulfonate group bonded to an aromatic ring wherein the functional groups are hydroxyl, carboxyl, or amino;

(c) at least one difunctional reactant selected from a glycol or a mixture of glycol and diamine having two —NRH groups, the glycol containing two —C(R$^1$)$_2$—OH groups wherein R in the reactant is hydrogen or an alkyl group of 1 to 6 carbon atoms, and R$^1$ in the reactant is a hydrogen atom, an alkyl of 1 to 5 carbon atoms, or an aryl group of 6 to 10 carbon atoms;

(d) 0 to about 40 mole percent of a difunctional reactant selected from hydroxycarboxylic acids having one —C(R—)$_2$—OH group, aminocarboxylic acids having one —NRH group, amino-alcohols having one —C(R—)$_2$—OH group and one —NRH group, or mixtures of said difunctional reactants wherein R in the reactant is hydrogen or an alkyl group of 1 to 6 carbon atoms; and (e) 1 to 40 mole percent of a "multifunctional" or "branch-inducing" reactant containing at least three functional groups selected from hydroxyl, carboxyl, amino, and mixtures thereof;

wherein all stated mole percents are based on the total of all acid, hydroxyl, and amino group containing reactants being equal to 200 mole percent, and wherein the polymer containing a portion of the acid-group containing reactants (100 mole percent acid) to hydroxyl and amino-group containing reactants (100 mole percent).

According to another embodiment, the branched water-dispersible sulfonated polyester condensation polymer comprises the reaction product of:

(I) at least one difunctional dicarboxylic acid which is not a sulfomonomer;

(II) about 2 to 15 mole percent, based on the total of all acid, hydroxyl and amino equivalence, of residues of at least one difunctional sulfomonomer containing at least one sulfonate group bonded to an aromatic ring wherein the functional groups are hydroxyl, carboxyl, or amino;

(III) at least one diol or a mixture of a diol and a diamine comprising:

(A) about 0.1 to 85 mole percent, based on the total mole percent of diol moieties or diol and diamine moieties, of a diol or diamine having the formula H(—OCH$_2$CH$_2$—)$_n$OH and HRN(—OH$_2$CH$_2$O—)$_n$ NHR wherein n is 2 to about 20 and R is hydrogen or C$_1$-C$_6$ alkyl provided that the mole percent of such moieties is inversely proportional to the value of n;

(B) about 0.1 to 15 mole percent, based on the total mole percent of diol moieties or diol and diamine moieties, of moieties of a poly(ethylene glycol) having the formula H(—OCH$_2$CH$_2$—)$_n$OH wherein n is 2 to about 500, provided that the mole percent of such moieties is inversely proportional to the value of n; and (C) 0 to greater than about 99 mole percent of the diol component or diol and diamine mixture being selected from the group consisting of a glycol and a mixture of glycol and diamine having two —NRH groups, the glycol containing two —C(R$^1$)$_2$—OH groups wherein R$^1$ in the reactant is a hydrogen atom, an alkyl of 1 to 5 carbon atoms, or an aryl group of 6 to 10 carbon atoms;

(IV) 0 to about 40 mole percent of a difunctional monomer reactant selected from the group consisting of hydroxycarboxylic acids having one —C(R—)$_2$—OH group, aminocarboxylic acids having one —NRH group, aminoalkanols having one —C(R—)$_2$OH group and one —NRH group and mixtures of said difunctional reactants wherein R in the reactant is hydrogen or an alkyl group of 1 to 6 carbon atoms; and (V) about 0.1 to 40 mole percent of a "multifunctional" or "branch-inducing" reactant containing at least three functional groups selected from hydroxyl, carboxyl, amino, and mixtures thereof;

the polymer containing substantially equal mole proportions of acid equivalents (100 mole percent) and diol or diol and diamine equivalents (100 mole percent).

Although the linear and branched polyesters of the present invention have different amounts of monomers and a different mix of groups of monomers, some specific groups of suitable monomers and preferred monomers of these groups are the same, as illustrated below.

The sulfonate-containing, water-dispersible adhesives and copolymers of this invention comprise polyesters, including polyesteramides, having repeating, alternating residues or moieties of one or more dicarboxylic acid which is not a sulfomonomer and one or more diols or a combination of one or more diols and one or more diamines wherein the mole percentages are based on 100 mole percent dicarboxylic acid residues and 100 mole percent diol or diol and diamine residues, for a total of 200 mole percent. Alternatively, the polyesters can include residues of monomers having mixed functionality such as hydroxycarboxylic acids, aminocarboxylic acids and/or aminoalkanols.

Examples of suitable difunctional dicarboxylic acid monomers used to make the residue of (I), (i), and (a) include aliphatic dicarboxylic acids, alicyclic dicarboxylic acids, aromatic dicarboxylic acids, or mixtures of two or more of these acids. Examples of suitable dicarboxylic acids include succinic; glutaric; adipic; azelaic; sebacic; fumaric; maleic; itaconic; 1,4-cyclohexanedicarboxylic; 1,3-cyclohexanedicarboxylic; phthalic; terephthalic; and isophthalic. If terephthalic acid is used as the dicarboxylic acid component of the polyester, superior results are achieved when at least 5 mole percent of one of the other acids is also used. It should be understood that the use of the corresponding acid anhydrides, esters, and acid chlorides of these acids is included in the term "dicarboxylic acid".

The difunctional sulfomonomer component of (II), (ii), and (b) can be a dicarboxylic acid or ester thereof containing a metal sulfonate group or a glycol containing a metal sulfonate group or a hydroxy acid containing metal sulfonate group. The cation of the sulfonate salt can be $NH_4^+$ or the metal ions $Li^+$, $Na^+$, $K^+$, $Mg^{2+}$, $Ca^{2+}$, $Cu^{2+}$, $Ni^{2+}$, $Fe^{2+}$, $Fe^{3+}$ and the like.

Residue or reactant (II), (ii), and (b) in the polyester of the present invention can be a difunctional monomer containing a —$SO_3M$ group attached to an aromatic nucleus, wherein M is hydrogen, $NH_4^+$, or a metal ion. The difunctional monomer component may be either a dicarboxylic acid or a diol adduct containing a —$SO_3M$ group. The cation of the sulfonate salt group can be $NH_4^+$, or the metal ions $Li^+$, $Na^+$, $K^+$, $Mg^{2+}$, $Ca^{2+}$, $Cu^{2+}$, $Ni^{2+}$, $Fe^{2+}$, $Fe^{3+}$ and the like. According to one embodiment wherein water stability of the polyester is desired, the cation of the sulfonated salt group can be a monovalent cation such as, for example, $NH_4^+$, $Li^+$, $Na^+$, or $K^+$.

The —$SO_3M$ group is attached to an aromatic nucleus, examples of which include benzene, naphthalene, anthracene, diphenyl, oxydiphenyl, sulfonyldiphenyl, and methylenediphenyl.

The cationic portion of a nonmetallic sulfonate group optionally present in reactant (II), (ii), and (b) is a nitrogen-based cation derived from nitrogen-containing bases which may be aliphatic, cycloaliphatic or aromatic basic compounds that have ionization constants in water at 25° C. of $10^{-3}$ to $10^{-10}$, preferably $10^{-5}$ to $10^{-8}$. Especially preferred nitrogen-containing bases are ammonia, dimethylethanolamine, iethanolamine, triethanolamine, pyridine, morpholine, and piperidine, due to availability, cost, and usefulness.

Reactant (II) can be present in a concentration in the range of about 4 to about 12 mole percent, about 6 to about 10 mole percent, or 8 mole percent. At amounts below about 4 mole percent the polyester can be less water soluble whereas at amounts above about 12 mole percent the polyester can be slightly too water-sensitive.

In accordance with one embodiment, reactant (ii) and, independently, reactant (b) can be present in an amount in the range of about 2 to about 25 mole percent, or 4 to 15 mole percent, based on the total acid equivalents.

Examples of preferred diols of (III) (A) and (iii) (A), due to availability, include diethylene glycol, triethylene glycol, and mixtures thereof. The concentration of (III) (A) can be in the range of from about 10 to about 80 mole percent, or 20 to 80 mole percent. At amounts outside this range, the polyesters can have lower softening points and higher Tg.

The moieties of (III) (A) and (iii) (A) can be the same as (III) (B) and (iii) (B), respectively, when the value n is low. According to one embodiment, (B) is a different moiety and is a poly(ethylene glycol). Examples of suitable poly(ethylene glycols) of (III) (B) and (iii) (B) include relatively high molecular weight polyethylene glycols, some of which are available commercially under the designation "Carbowax", a product of Union Carbide. Poly(ethylene glycols) having molecular weights of from about 500 to about 5000 are especially suitable.

The moieties of (B) are preferably at a concentration of about 1 to 5 mole percent, particularly when n is 10 to 30, due to the preferably higher softening points. The remaining portion of the glycol component of (III), (iii), and (c) can consist of aliphatic, alicyclic, and aralkyl glycols. Examples of these glycols include neopentyl glycol; ethylene glycol; propylene glycol; 1,3-propanediol; 2,4-dimethyl-2-ethyl-hexane-1,3-diol; 2,2-dimethyl-1,3-propanediol; 2-ethyl-2-butyl-1,3-propanediol; 2-ethyl-2-isobutyl-1,3-propanediol; 1,3-butanediol; 1,4-butanediol; 1,5-pentanediol; 1,6-hexanediol; 2,2,4-trimethyl-1,6-hexanediol; thiodiethanol; 1,2-cyclohexanedimethanol; 1,3-cyclohexanedimethanol; 1,4-cyclohexanedimethanol; 2,2,4,4-tetramethyl-1,3-cyclobutanediol; p-xylylenediol and neopentyl glycol. Polyesters may be prepared from two or more of the above glycols. Preferred glycols, due to availability, cost, and usefulness, include neopentyl glycol, ethylene glycol, 1,3-propane diol, 1,4-butane diol, 1,6-hexane diol and cyclohexane dimethanols.

Examples of difunctional monomer component of (III) and (c) which are diamines include ethylenediamine; hexamethylenediamine; 2,2,4-trimethylhexa-methylenediamine; 4-oxaheptane-1,4-diamine, 4,7-dioxadecane-1,10-diamine; 1,4-cyclohexanebismethylamine; 1,3-cyclohexanebismethylamine; heptamethylenediamine; dodeca-methylenediamine, etc.

The amount of the moieties III (C) can be selected to optimize the Tg and the softening point of the polymer. The moieties III (C) can be present in the polyester in the range of from about 0 to about 99 mole percent, about 20 to about 80 mole percent, or 30 to 70 mole percent.

Difunctional components which are aminoalcohols or aminoalkanols include aromatic, aliphatic, heterocyclic, and other types in regard to component (IV), (iv) and (d). Specific examples include 5-aminopentanol-1,4-aminomethylcyclohexanemethanol, 5-amino-2-ethyl-pentanol-1,2-(4-beta-hydroxyethoxyphenyl)-1-aminoethane, 3-amino-2,2-di-methylpropanol, hydroxyl-ethylamine, etc. Generally these aminoalcohols contain from 2 to 20 carbon atoms, one —NRH group and one —$CR_2$—OH group.

Difunctional monomer components which are aminocarboxylic acids include aromatic, aliphatic, heterocyclic, and other types in regard to component (IV), (iv), and (d) and include lactams. Specific examples include 6-aminocaproic acid, its lactam known as caprolactam, omega aminoundecanoic acid, 3-amino-2-dimethylpropionic acid, 4-(beta-aminoethyl)benzoic acid, 2-(beta-aminopropoxy)benzoic acid, 4-aminomethylcyclo-hexanecarboxylic acid, 2-(beta-aminopropoxy)cyclohexanecarboxylic acid, etc. Generally, these compounds contain from 2 to 20 carbon atoms.

These moieties (IV) (iv) and (d) are less preferred, due to cost and performance, but they can be present. The concentration of these moieties can be in the range of less than about 20 mole percent, less than about 10 mole percent, or 0 mole percent.

The polyester compositions are branched by virtue of the presence of a multifunctional reactant (V) and (e) that contains at least three functional groups selected from hydroxyl, carboxyl, and amino. Examples of preferred multifunctional reactants of (V) and (e) are trimethylpropane (TMP), trimethylolethane (TME), glycerole, pentaerythritol, erythritol, threitol, dipentaerythritol, sorbitol, trimellitic anhydride, pyromellitic dianhydride, and dimethylolpropionic acid. According to one embodiment, TMP can be used, due to availability and effective results.

The amount of this branching agent (V) and (e) can be in the range of from about 0 mole percent to about 20 mole percent, about 0.1 mole percent to about 10 mole percent, or 1 mole percent to 7 mole percent. At very high amounts of branching agent the polyester can be prone to gelation whereas at low amounts, the polyester can have properties that lead to poor performance.

In one embodiment, the polycondensation reactant conditions for the preparation of the polyester can be at a temperature of 150° C. to 230° C. in the presence of a catalyst. The catalyst for the polycondensation reaction can be an acid catalyst. According to one embodiment, the catalyst can be an organometallic compound, such as a tin or titanium containing compound. Suitable examples of the acid catalyst include dibutyltinoxide, stannous oxalate, titaniumtetraisopropoxide, butylstannoic acid, and p-toluenesulfonic acid, with butylstannoic acid being most preferred. According to one embodiment, a butylstannoic acid catalyst is present in an amount in the range of from about 0 to about 0.5 weight percent, about 0.01 to about 0.2 weight percent, or 0.1 weight percent, based on the total weight of reactants.

In accordance with one embodiment of the present invention, the adhesive composition comprises one or more sulfonated polyesters comprise in an amount greater than about 80 weight percent, greater than about 90 weight percent, or greater than 95 weight percent of the total adhesive composition. In one embodiment, the adhesive comprises a blend of one linear and one branched sulfonated polyester, which constitutes at least 98 weight percent of the total adhesive composition.

The values for properties of the polyesters of the present invention, such as, for example, tack, glass transition temperature (Tg), inherent viscosity, molecular weight, and the like can vary widely. In accordance with one embodiment of the present invention, wherein the adhesive composition comprises a blend of two or more sulfonated polyesters, the relative weight ratio of the individual polymers can also vary greatly. Ultimately, the individual polyesters can be selected and/or blended to achieve the properties of the final adhesive composition, such as, for example, Tg. Ranges for properties of the inventive adhesive composition will be discussed in detail shortly.

The adhesive composition of the present invention also comprises a humectant in physical mixture with the sulfonated polyester or polyesters. As used herein, the term "humectant" refers to a hygroscopic compound capable of maintaining the moisture content of a composition within a narrow range over extended periods of time despite broad fluctuations in external relative humidity. In accordance with one embodiment of the present invention, a humectant can be present in an amount in the range of from about 0.01 to about 20 weight percent, about 0.5 to 10 weight percent, or 1 to 4 weight percent of the total adhesive composition.

In general, humectants can be inorganic, organic, or metallo-organic. Examples of humectants include, but are not limited to, calcium chloride, glucuronic acid, lactic acid, urea, acetamide MEA, sodium aspartate, sodium lactate, polyethylene glycol, diethylene glycol, triethylene glycol, 1,3-butadiol, 1,2,6-hexanetriaol, dipropylene glycol, propylene glycol, ethylene glycol, glycerol, sorbitol, xylitol, sucrose, fructose, glucose, maltose, corn syrup, natural honey and any mixtures thereof. According to one embodiment, organic humectants with multiple hydroxyl functionality (e.g., polyols) can be employed in the inventive adhesive composition. In another embodiment, the humectant of the inventive adhesive comprises propylene glycol, ethylene glycol, and/or glycerol.

Generally, a humectant can be characterized according to the amount of water it absorbs from the environment at a constant relative humidity and temperature. According to one embodiment, the humectant of the inventive composition can absorb water in the range of from about 6 to about 30 percent water, from about 7 to about 27 percent water, or 8 to 25 percent water by weight of the adhesive composition at 50% relative humidity (RH) and a temperature between 70 and 80° F. In contrast, under similar conditions, common plasticizers typically absorb less than about 5 weight percent water.

The molecular weight and crystalline structure of the humectant can impact the final properties of the adhesive compositions. In general, the addition of crystalline humectants causes the glass transition temperature of the adhesive composition to increase, which results in a more brittle, less flexible adhesive. According to one embodiment, the humectant of the present invention can be non-crystalline and have a molecular weight less than about 1,500 grams per mole, less than about 1,000 grams per mole, less than about 750 grams per mole, or less than 150 grams per mole.

In addition, the humectant of the inventive adhesive does not irritate skin. A comprehensive list of chemical compounds approved for skin contact are included on the United States Food and Drug Administration's Generally Recognized as Safe (GRAS) list of chemicals approved for skin contact. The GRAS list can be accessed on the World Wide Web at http://vm.cfsan.fda.gov/~dms/eafus.html. In one embodiment, the humectant of the adhesive blend can be listed on the GRAS list.

The adhesive composition of the present invention optionally comprises a pH modifier. In one embodiment, pH modifier can be added in an amount sufficient to adjust the final pH of the adhesive blend to be in the range of from about 6.0 to about 8.5, or about 6.5 to about 8.25, or 7 to 8. Examples of pH modifiers suitable for use in the inventive composition include, but are not limited to, sodium hydroxide, potassium hydroxide, methylamine, ethylamine, propylamine, di-methylamine, diethylamine, dipropylamine, trimethylamine, triethylamine, tripropylamine, monomethanolamine, monoethanolamine, monopropanolamine, dimethanol-amine, diethanolamine, diprpopanolamine, trimethanolamine, triethanolamine, tripropanol-amine, citrate buffer, phosphate buffer, glycine buffer, acetate buffer, other buffer or the like.

The adhesive composition of the present invention can comprise additives other than the sulfonated polyester or polyesters, humectant, and optional pH modifier. In one embodiment, the adhesive blend additionally includes one or more tackifiers and/or plasticizers. Tackifiers increase the Tg of the adhesive, which increases the softening point in order to prevent cold flow. Plasticizers lower the Tg, which increases the flexibility and durability of an adhesive. In one embodiment, the adhesive blend comprises in the range of from about 0 to about 10 weight percent, about 0 to about 4 weight percent, or 0 to 1 weight percent of the total adhesive composition of one or more tackifiers and/or plasticizers. In another embodiment, the inventive adhesive includes substantially no tackifiers and/or plasticizers because the properties and amounts of the sulfonated polyester or polyesters can be selected and/or adjusted to regulate the Tg and other properties of the final composition.

In addition, modifiers such as waxes, cold flow reducing agents, and polymers other than water-dispersible sulfonated polyesters may be added to the inventive adhesive formulation. In one embodiment, polyethylene glycol with a molecular weight less than about 1,500 grams per mole, less than about 1,000 grams per mole, less than about 750 grams per mole, or less than 150 grams per mole and a melting point less than about 40° C. or less than 35° C. can be added to the adhesive blend as a cold flow reducing agent. In another embodiment, the inventive adhesive blend may comprise polymers other than the water-dispersible sulfonated polyesters, such as hydrophilic and/or hydrophobic polymers. Further, other additives such as UV light absorbers, nucleating agents, colorants, pigments, solvents, fillers, cross-linking and/or radiation-curable agents, photoinitiators, viscosity modifiers, and surfactants can be present in small amounts as needed. The adhesive composition of the present invention may comprise in the range of from about 0 to about 20 weight percent, about 0 to about 10 weight percent, about 0 to about 4 weight percent, or 0 to 0.99 weight percent of one or more of the waxes, cold flow reducing agents, polymers other than water-dispersible sulfonated polyesters, and one or more of the additives discussed in the preceding paragraph.

The adhesive composition may additionally include one or more compounds to control its physical properties such as, for example, dispersibility in water or other liquids. In one embodiment, the dispersibility control agent can be a salt. As used herein, the term "salt" refers to an ionic compound with overall charge neutrality. In another embodiment, the dispersibility control agent can be sodium chloride (NaCl). According to one embodiment, the adhesive blend comprises in the range of about 0 to about 10 weight percent, about 0 to about 5 weight percent, about 0 to about 3 weight percent, or about 0 to about 1 weight percent of a dispersibility control agent. In accordance with one embodiment, the adhesive composition of the present invention can be about 10 percent, about 25 percent, about 50 percent, about 75 percent, about 95 percent, about 99 percent, or completely dispersible in a liquid comprising water. The adhesive composition of the present invention may also comprise one or more modifiers added to the adhesive for its use in specific medical applications. According to one embodiment, the adhesive composition may comprise one or more pharmaceutical components for transdermal drug delivery. In accordance with another embodiment, the adhesive of the present invention can comprise an antimicrobial and/or antibacterial agent. According to a further embodiment, the adhesive can contain a chemical ingredient to expedite wound healing. In accordance with yet another embodiment, the adhesive may be made conductive according to any means known in the art for use in medical articles such as biomedical electrodes and other applications wherein a conductive adhesive can be advantageous.

The adhesive composition of the present invention can be hypoallergenic because its components are non-skin irritants. The polyesters and humectants of the present adhesive composition comprise in the range of from about 0 to about 10 mole percent, about 0 to about 2, or 0 to 1 mole percent of compounds that can irritate skin, such as, for example acrylic and/or latex. According to one embodiment, the polyester or polyesters of the adhesive composition contain in the range of from about 0 to about 15 mole percent latex and/or acrylic moieties, about 0 to about 10 mole percent latex and/or acrylic moieties, about 0 to about 5 mole percent latex and/or acrylic moieties, or 0 to 4 mole percent latex and/or acrylic moieties. In another embodiment, sulfonated polyesters of the present invention comprise substantially no acrylic or latex moieties. In a further embodiment, the polyesters and humectants of the present invention can be recognized by the Food and Drug Administration's Generally Recognized as Safe (GRAS) list and are approved for skin contact. According to one embodiment, the adhesive of the present invention can be used for articles, including medical articles, for attachment to the skin of individuals with latex and/or acrylic allergies without triggering an allergic reaction.

As described in detail below, the characteristics and performance of the inventive adhesive blend can be defined in terms of glass transition temperature (Tg), hold power, loop tack, moisture mass uptake (MMU), and switchability.

The glass transition temperature of an adhesive blend is an indicator of the low-temperature performance of a PSA. Adhesives with low glass transition temperatures possess good tack, but tend to cold flow, which increases the tendency of adhesive articles employing the composition to creep. Adhesives with high glass transition temperature resist cold flow, but tend to be brittle and less tacky. In one embodiment, the adhesive composition of the present invention has a glass transition temperature in the range of from about −10 to about 15° C., or 6 to 10° C. In one embodiment, the Tg of an inventive blend comprising a blend of two sulfonated polyesters can be controlled by adjusting the relative amounts of water-dispersible sulfonated polyesters having widely varying individual glass transition temperatures. Typically, Differential Scanning Calorimetry (DSC) or Dynamic Mechanical Analysis (DMA) is used to measure an adhesive's glass transition temperature.

Hold power measures the amount of time that an adhesive attached to a substrate can withstand the force of a static weight before undergoing shear failure. In general, stronger adhesives have longer hold times. In one embodiment, the inventive PSA has a hold time greater than about 20 minutes, greater than about 30 minutes, or greater than about 50 minutes, as measured in accordance with the procedure outlined in Pressure Sensitive Tape Council (PSTC) 17.

Loop tack is one method used to measure the ability of a PSA to remain adhered to a surface. In one embodiment, the loop tack of the inventive adhesive blend is in the range of from about 0.01 to about 10 pound-force per inch (lbf/in), about 1 to about 7 lbf/in, or 1.2 to 5 lbf/in, as determined according to the procedure disclosed in PSTC-16. Specific values for hold power and loop tack for several inventive adhesive blends are presented in Example 2 of the subsequent Examples section.

The moisture mass uptake (MMU) of an adhesive measures its ability to absorb and retain moisture from its environment. In one embodiment, the inventive adhesive blend has a moisture mass uptake greater than about 4.5 weight percent, greater than about 6 weight percent, or greater than 8 percent, as determined according to the procedure outlined in Example 3 of the subsequent Examples section.

In one embodiment of the present invention, the PSA is "switchable." As used herein, the term "switchable" refers to the ability of an adhesive to undergo a reduction in peel strength upon contact with a low-ion liquid. Peel strength, as defined herein, refers to the force per unit width required to remove an adhesive from a substrate at an angle of 180°, as be determined according to the procedure outlined in PSTC-101. Peel strength is classified herein according to the substrate from which the adhesive is stripped: "standard peel strength" refers to the peel strength measured using a stainless steel substrate and "skin peel strength" refers to the peel strength measured using the skin of a wearer's forearm as a substrate.

Regardless of the substrate, the reduction in peel strength can be defined according to the following equation: (average dry peel strength−average wet peel strength)/(average dry peel strength), expressed as a percentage. As used herein, the term "dry peel strength" refers to the peel strength of an adhesive prior to contact with a low-ion liquid, averaged over the length of the adhesive article removed and "average wet peel strength" refers to the peel strength, averaged over the length of the removed adhesive article, of the PSA after contact with a low-ion liquid.

In one embodiment, the adhesive composition has an average dry standard peel strength of greater than about 5 pound-force per inch (lbf/in), greater than about 10 lbf/in, or greater than 15 lbf/in and an average wet standard peel strength of less than about 4 lbf/in, less than about 3.5 lbf/in, or less than 3.0 lbf/in. In accordance with another embodiment, the average wet standard peel strength can be less than about 75 percent, less than about 50 percent, or less than about 35 percent of the average dry standard peel strength. As a result, the inventive adhesive blend can undergo a reduction in average standard peel strength of greater than about 25 percent, greater than about 50 percent, or greater than 65 percent.

In yet another embodiment, the inventive adhesive can have an average dry skin peel strength of greater than about 0.1 lbf/in, greater than about 0.5 lbf/in, or greater than 1 lbf/in and an average wet skin peel strength of less than about 0.09 lbf/in, less than about 0.05 lbf/in, or less than 0.01 lbf/in. In one embodiment, the average wet skin peel strength of the inventive composition can be less than about 50 percent, less than about 25 percent, less than about 10 percent, or less than 5 percent of the average dry skin peel strength of the adhesive blend. Correspondingly, inventive adhesive blend experiences a reduction in average skin peel strength of greater than about 50 percent, greater than about 75 percent, greater than about 90 percent, or greater than 95 percent.

In one embodiment, the switchability of the inventive adhesive can be activated by contacting it with a low-ion liquid. As used herein, the term "low-ion liquid" refers to a liquid having an ion content of less than about 5 grams per liter (g/L), less than about 1.5 g/L, or less than 0.1 g/L of ions. In one embodiment, the low-ion liquid can be a polar liquid. In another embodiment, the low-ion liquid can comprise water. The duration and method of contacting the switchable adhesive article with a low-ion liquid can vary widely according to the size, location, shape, dwell time, and other similar properties of the adhesive article and substrate. In the embodiment wherein the inventive article is attached to skin, the duration and method of low-ion liquid contact additionally depend on the location of the article, the sensitivity of the wearer's skin, and other related factors.

In one embodiment, the switchable adhesive composition can be used in an aqueous adhesive solution applied via spray to skin or other substrate, such as, for example, steel or other surface. In another embodiment, the inventive blend adhesive can be applied to any suitable backing known to the art to create a switchable adhesive article. In general, the two-sided backing provides both structural integrity for the adhesive and protection for the substrate. The backing itself can be absorbent and/or can employ absorbent materials. The backing used in the adhesive article of the present invention can be substantially elastic (e.g., bandages) or substantially inelastic (e.g., tapes). It can be reinforced for additional strength by organic or inorganic materials or by any method or pattern of construction or adhesive application known in the art.

The backing employed in the adhesive article of the present invention can be composed of any woven or non-woven, natural or synthetic material that is compatible with the skin, such as, for example, cotton, viscose, silk, polymer, or fibers. According to one embodiment, the backing of the article of the present invention can be hypoallergenic. In one embodiment, the backing is sufficiently porous so as to be permeable to air and water vapor and, further, to provide a pathway for the low-ion liquid to directly contact the adhesive. The backing may be easily moldable for comfort and yet possess sufficient strength and limited extensibility so as to be durable. Further, the backing should be compatible with the adhesive composition to the extent that the composition forms a bond with one side of the backing in a way that limits the adhesive's tendency to undergo cohesive failure.

The PSA composition can be applied to the backing as a liquid dispersion (aqueous or solvent) or via hot melt application methods. When applied as a solution, the adhesive compositions can generally be applied by conventional processes well-known to the art, such as extrusion coating, spray coating, roll coating, brush coating, knife coating, dip coating, etc. In addition, the article may undergo additional processing required for its final use, such as, for example, lamination.

In this application, the inventive switchable adhesive article can be used by applying the article to skin or other delicate surface and securing it with nominal pressure. In one embodiment, prior to removal, the switchable adhesive article can be contacted with a low-ion liquid in order to activate its switchability. Subsequently, the article can be removed from the substrate. For example, the switchable adhesive article can be adhered to the substrate using nominal finger pressure. Thereafter, a low-ion liquid with the above-mentioned properties can be applied to the article in such as way as to contact the adhesive, thereby causing the reduction in standard peel strength or skin peel strength as discussed previously. As previously mentioned, the specific liquid contact time and method of contact depend on the article's size, shape, construction, location, and dwell time. In general, the larger, more rigid articles with extensive dwell times require a longer contact time and more intimate method of contact, such as, for example, direct soaking. Other contact methods can include, for example, wetting, saturating by means of another wetted article such as a cloth, spraying, showering, or any other appropriate means of allowing the low-ion liquid to travel through the sufficiently porous backing in order to contact the adhesive and enact its switchability. Once the adhesive has been switched, the article can then be removed in a way that avoids damage or trauma to the affected area. In one embodiment, the adhesive composition may include an indicator, such as, for example a color-change indicator, signifying when the adhesive has undergone a reduction in peel strength. Additionally, if adhesive remains on the substrate after the article is removed, the residual can be rinsed away with additional low-ion fluid.

Although the present invention has been described above with reference to its use in medical applications, it should be apparent that the compositions, articles, and methods of the present invention can be adapted for other uses, especially when it is desirable to minimize substrate damage upon removal of an adhesive article. In one embodiment, present invention may be employed in temporary adhesive articles and/or compositions, wherein total removal of the article and adhesive from the substrate is desirable. For example, the present invention can be modified for uses, such as, for example, as a label, tape, sticker, or other adhesive article attached to a delicate surface such as, for example, ceramic, porcelain, glass, and the like. Also, the articles and methods of the present invention can be used on substrates that are not suitable for contact with solvents, such as, for example, kitchenware. In addition, the water-dispersible nature of the present invention causes it to be highly repulpable, making it suitable for use in recyclable adhesive articles.

EXAMPLES

The following examples are intended to be illustrative of the present invention in order to teach one of ordinary skill in the art to make and use the invention and are not intended to limit the scope of the invention in any way.

Example 1

Preparation of Adhesive Blends

This example demonstrates the preparation of several control, comparative, and inventive adhesive blends.

The adhesive compositions in the following examples include a blend of one branched sulfonated polyester (commercially available from Eastman Chemical Company in Kingsport, Tenn., under the product designation AQ1045™) and one linear sulfonated polyester (commercially available from Eastman Chemical Company, under the product designation AQ55S™).

Control blend 1 was prepared by melting 240.00 grams of the above-described linear sulfonated polyester in a one-pint steel can at a temperature of 205° C. (400° F.). Next, 60.00 grams of the above-mentioned branched sulfonated polyester were added and the resulting blend comprising a 4:1 weight ratio of branched-to-linear sulfonated polyester was mixed for 30 minutes using a spiralwire mixing blade coupled to a stainless steel shaft agitator. The contents of the container were poured onto release paper and allowed to cool on a lab bench under ambient conditions for a period of 24 hours. Control blends 2, 3, and 4 were prepared in a similar manner, but with branched-to-linear polymer weight ratios of 2:1, 6:1, and 8:1, respectively, as shown in Table 1 below.

Comparative blends 5 and 6 were prepared with a 4:1 weight branched-to-linear polymer ratio in a similar manner to control blend 1. Comparative blend 5 and comparative blend 6 additionally included 2 weight percent (6.0 grams) and 6 weight percent (18.0 grams), respectively, of glycerol triacetate, a common plasticizer commercially available from Eastman Chemical Company, under the product designation TRIACETIN™. Similarly, Comparative blends 7 and 8 were prepared with a 4:1 polymer weight ratio like Control blend 1, but additionally included 2 weight percent (6.0 grams) and 6 weight percent (18.0 grams), respectively, of dipropylene glycerol dibenzoate, another common plasticizer, commercially available from Velsicol Chemical Corporation, under the product designation BENZOFLEX® 9-88. Procedurally, the plasticizer was added prior to mixing along with the branched sulfonated polyester and the resulting blend was processed according to the procedure previously described for Control blends 1-4.

Inventive blends 9-12 and Inventive blends 13-16 were prepared with varying polymer weight ratios, analogously to Control blends 1-4, but additionally included 2 weight percent (6.0 grams) and 6 weight percent (18.0 grams), respectively, of the humectant glycerol. Table 1 below summarizes the compositions of the control, comparative, and inventive adhesive blends described above.

TABLE 1

Adhesive Blend Compositions

| | Blend Type | Polymer Ratio | Polymer, wt % | Additive, wt % | Additive |
|---|---|---|---|---|---|
| 1 | Control | 2:1 | 100 | 0 | — |
| 2 | Control | 4:1 | 100 | 0 | — |
| 3 | Control | 6:1 | 100 | 0 | — |
| 4 | Control | 8:1 | 100 | 0 | — |
| 5 | Comparative | 4:1 | 98 | 2 | TRIACETIN ™ |
| 6 | Comparative | 4:1 | 94 | 6 | TRIACETIN ™ |
| 7 | Comparative | 4:1 | 98 | 2 | BENZOFLEX ® 9-88 |
| 8 | Comparative | 4:1 | 94 | 6 | BENZOFLEX ® 9-88 |
| 9 | Inventive | 2:1 | 98 | 2 | GLYCEROL |
| 10 | Inventive | 4:1 | 98 | 2 | GLYCEROL |
| 11 | Inventive | 6:1 | 98 | 2 | GLYCEROL |
| 12 | Inventive | 8:1 | 98 | 2 | GLYCEROL |
| 13 | Inventive | 2:1 | 94 | 6 | GLYCEROL |
| 14 | Inventive | 4:1 | 94 | 6 | GLYCEROL |
| 15 | Inventive | 6:1 | 94 | 6 | GLYCEROL |
| 16 | Inventive | 8:1 | 94 | 6 | GLYCEROL |

Example 2

Properties of Adhesive Blends

Values for average dry peel strength, loop tack, and hold power were determined for Control blends 1-4 and Inventive blends 9-16. Table 2 below presents the results.

Loop tack was determined in accordance with the procedure described in PSTC-16. Hold Power was determined in accordance with the procedure described in PSTC-107. Table 2 below presents the results for loop tack and hold power for Control blends 1-4 and Inventive blends 9-16.

TABLE 2

Properties of Control Blends 1–4 and Inventive Blends 9–16

| Blend | Loop Tack, lbf/in | Hold Power, min |
|---|---|---|
| 1 | 0.01 | 0 |
| 2 | 0.02 | 57 |
| 3 | 0.28 | 170 |
| 4 | 0.08 | 38 |
| 9 | 0.10 | 2451 |
| 10 | 0.80 | 171 |
| 11 | 2.43 | 148 |
| 12 | 1.93 | 149 |
| 13 | 0.11 | 334 |
| 14 | 4.68 | 95 |
| 15 | 1.24 | 65 |
| 16 | 1.10 | 102 |

Example 3

Utility of a Humectant in the Inventive Adhesive Blend

This example illustrates the utility of a humectant in the inventive adhesive blend.

The moisture mass uptake measures the amount of moisture an adhesive blend is capable of absorbing. To test the moisture mass uptake of Control blend 2, Comparative blends 5-8, and Inventive blends 10 and 14, each composition was prepared according to the procedure described in Example 1. However, instead of release paper, approximately 0.4 grams of a molten sample of each blend was transferred on an 80-mm diameter aluminum pan. The samples were then allowed to cool for 24 hours under ambient conditions on a lab bench. The samples were then placed in a vacuum oven at 50° C. for 8 hours under a vacuum of 508 mm (20 inches) Hg with a nitrogen sweep and then for 16 hours at 50° C. under a vacuum of 712 mm (28 inches) Hg with no nitrogen sweep in order to thoroughly dry the samples. The conditioned samples were weighed and then placed into a humidity chamber at 100% relative humidity and 23° C. (75° F.) for a period of 24 hours. The final weight of each blend after exposure to the previously-described environment was recorded. The moisture mass uptake was determined according to the following formula: (final wet weight−initial dry weight)/(final wet weight), expressed as a percentage.

Next, the loop tack of Control blend 2, Comparative blends 5-8, and Inventive blends 10 and 14 were determined. Loop tack measures the ability of an adhesive to remain adhered to a substrate. First, adhesive strips were created by coating a 1.0-mil layer of each blend onto 2.0 mil thick Mylar backing using a knife coater heated to 150° C. (302° F.). The adhesive-coated backing was allowed to cool before it was cut into 2.5 mm×17.5 mm strips. The loop tack of each blend was then determined according to the procedure described in PSTC-16. The crosshead displacement rate was 300 mm (12 inches) per minute with an initial distance from the top of the loop to the stainless steel plate of 2 inches. The maximum displacement was 1.75 inches and the dwell time was 1 second.

Table 3 summarizes the results for moisture mass uptake and loop tack for Control blend 2, Comparative blends 5-8, and Inventive blends 10 and 14.

TABLE 3

Moisture Mass Uptake and Loop Tack for Blends 2, 5–8, 10 and 14

| Blend | Type | Adhesive Blend Additive, wt % | Additive Used | Moisture Mass Uptake, wt % | Loop Tack, lbf/in |
|---|---|---|---|---|---|
| 2 | Control | 0 | — | 4.20 | 0.02 |
| 5 | Comparative | 2 | TRIACETIN ™ | 3.60 | 0.04 |
| 6 | Comparative | 6 | TRIACETIN ™ | 4.10 | 0.52 |
| 7 | Comparative | 2 | BENZOFLEX ® 9-88 | 3.60 | 0.08 |
| 8 | Comparative | 6 | BENZOFLEX ® 9-88 | 3.20 | 0.44 |
| 10 | Inventive | 2 | GLYCEROL | 9.10 | 0.80 |
| 14 | Inventive | 6 | GLYCEROL | 14.00 | 4.70 |

According to the results presented in Table 3, Inventive blends 10 and 14, which employ a humectant in lieu of a common plasticizer, absorb more moisture and have a higher loop tack than Comparative blends 5-8, which employ common plasticizers.

Example 4

Switchability of Inventive Adhesive on Steel

The following example demonstrates the switchability of the inventive adhesive when applied to a stainless steel substrate. Switchability of the inventive adhesive on steel refers to its reduction in standard peel strength upon contact with a low-ion liquid.

Inventive blend 10, which comprised a 4:1 weight ratio of branched to linear sulfonated polyester and 2 weight percent glycerol, was prepared according to the procedure described in Example 1. The adhesive was then incorporated into an adhesive tape by coating the blend onto a 2.0 mil thick Mylar backing according to the procedure in Example 2. The tape was then cut into 5-mm (0.2-in) wide strips and adhered to a 40 mm×125 mm×1.3 mm (1.6 in×4.9 in×0.05 in) stainless steel plate with four passes of a hand-operated 2-lb roller as described in PSTC 101. After a dwell time of 10 minutes, the adhesive strips were removed with a UTM at a cross-head displacement rate of 300 mm (12 inches) per minute at an angle 180°. The resulting average dry standard peel strength was recorded.

To measure the average standard wet peel strength, additional pressure sensitive tape strips employing Inventive blend 14 were applied to a stainless steel plate as previously described. The plate was then completely submersed in a bath of deionized water for a period of 1 hour. The plate was removed from the bath and the average wet peel strength of the adhesive strips was determined in a similar manner to the average dry peel strength as described above. Table 4 below summarizes the results.

TABLE 4

Switchability of Inventive Adhesive on Steel (Standard Peel Strength)

| Property | Value |
|---|---|
| Average Dry Standard Peel Strength, lbf/in | 7.0 |
| Average Wet Standard Peel Strength, lbf/in | 2.0 |
| Average Reduction in Standard Peel Strength, % | 71.4 |

As illustrated by the reduction in standard peel strength results presented in Table 4, the inventive adhesive composition is switchable when adhered to a stainless steel substrate upon contact with a low-ion liquid such as de-ionized water.

Example 5

Switchability of Inventive Adhesive on Skin

The following example demonstrates the switchability of the inventive adhesive when applied to skin. Switchability on skin refers to the reduction in skin peel strength of the inventive adhesive.

Inventive blend 14 was prepared as described previously in Example 1. The molten blend was coated onto release paper using a 1-mil gap doctor blade heated to 205° C. (400° F.). The 17.0-mil thick cloth backing, which was composed of 8 mil diameter fibers and had a weight of 0.011 g/yard, was then pressed onto the cool adhesive and secured using a pinch roller-type laminator. Adhesive test strips 12 inches long (300 mm) and 0.5 inches wide (12.7 mm) were cut and adhered to the skin of the wearer's forearm. The strips were secured with four passes of a 2-lb hand-operated roller as described in the procedure outlined in PSTC-101.

After a dwell time of 10 minutes, the article was removed by an Instron 4201 UTM at an angle of 180° from the skin at a cross-head displacement rate of 300 mm (12 inches) per minute. The resulting average dry skin peel strength was recorded.

To determine the average wet skin peel strength, a cloth towel saturated with deionized water was placed over the entire surface area of the article for a period of 30 minutes. After 30 minutes, the cloth was removed and the tape was stripped from the skin by the UTM at a rate of 300 mm (12 inches) per minute at an angle of 180°. The resulting average wet skin peel strength as well as the average dry skin peel strength and the average skin peel strength reduction are presented in Table 5 below.

TABLE 5

Switchability of Inventive Blend on Skin (Skin Peel Strength)

| Property | Value |
|---|---|
| Average Dry Skin Peel Strength, lbf/in | 0.35 |
| Average Wet Skin Peel Strength, lbf/in | 0.00 |
| Average Reduction in Skin Peel Strength, % | 100 |

As illustrated by the reduction in skin peel strength results presented in Table 5, the inventive adhesive composition is switchable when adhered to skin upon contact with a low-ion fluid such as de-ionized water.

Example 6

Controlling Dispersibility of Inventive Adhesive

The following example illustrates the effect of a dispersibility control agent on the inventive adhesive blend.

Four samples of Inventive blend 10 were prepared according to the procedure described in Example 1 and an additional 1, 3, 5, and 10 weight percent of sodium chloride (NaCl) was added to create Inventive blends 17, 18, 19, and 20, respectively. The blends were allowed to cool as described in Example 1 prior to being cut into 1-inch disks. The samples were then submerged in 50 mL of de-ionized water for a period of 1 hour. The relative dispersibility of each the samples were visually observed with the following results:

Inventive blend 17 (1 wt % NaCl) was almost completely dispersed, as evident by the cloudy water, and the original sample shape was not distinguishable.

Inventive blend 18 (3 wt % NaCl) had started to disperse, but retained most of its original shape. This sample was very swollen.

Inventive blend 19 (5 wt % NaCl) was moderately swollen, but was closer to its original shape than Inventive blend 18. The edges of the sample appeared to be dispersing slightly.

Inventive blend 20 (10 wt % NaCl) was only slightly swollen, but was very similar to its original shape and did not seem to have dispersed greatly.

The results of this example demonstrate that incorporating up to 10 weight percent of a salt can affect the degree of water-dispersibility of the inventive adhesive composition.

DEFINITIONS

As used herein, the terms "a," "an," "the," and "said" means one or more.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the term "amphiphilic" refers to a material that has both hydrophilic and hydrophobic properties.

As used herein, the term "average dry skin peel strength" refers to the average force per unit width required to remove an adhesive and/or adhesive article from a wearer's skin at a 180° angle, relative to the wearer's skin, in the absence of the adhesive being switched with a low-ion liquid. Skin peel strength can be determined in accordance with the procedure described in Example 5.

As used herein, the term "average dry standard peel strength" refers to the average force per unit width required to remove an adhesive and/or adhesive article from a stainless steel substrate at a 180° angle, relative to the substrate, in the absence of contact with a low-ion liquid. Standard peel strength can be determined according to the modified procedure in PSTC-101 as described in Example 4.

As used herein, the term "average skin peel strength" refers to the average force per area width required to remove an adhesive and/or adhesive article from a wearer's skin at a 180° angle, relative to the wearer's skin, averaged over the length of the article. Skin peel strength can be determined in accordance with the procedure described in Example 5.

As used herein, the term "average standard peel strength" refers to the average force per unit width required to remove an adhesive and/or adhesive article from a stainless steel substrate at a 180° angle, relative to the substrate, averaged over the length of the article. Standard peel strength can be determined according to the modified procedure in PSTC-101 as described in Example 4.

As used herein, the term "average wet skin peel strength" refers to the average force per unit width required to remove an adhesive and/or adhesive article from a wearer's skin at a 180° angle, relative to the wearer's skin, after the adhesive was contacted with a low-ion liquid. Skin peel strength can be determined in accordance with the procedure in Example 5.

As used herein, the term "average wet standard peel strength" refers to the average force per unit width required to remove an adhesive and/or adhesive article from a stainless steel substrate at a 180° angle, relative to the substrate, after the adhesive was contacted with a low-ion liquid. Standard peel strength can be determined according to the modified procedure in PSTC-101 as described in Example 4.

As used herein, the term "cold flow reducing agent" refers to a material added to an adhesive composition to reduce the tendency of an adhesive to cold flow.

As used herein, the terms "comprising," "comprises," and "comprise" are open-ended transition terms used to transition from a subject recited before the term to one or elements recited after the term, where the element or elements listed after the transition term are not necessarily the only elements that make up of the subject.

As used herein, the terms "containing," "contains," and "contain" have the same open-ended meaning as "comprising," "comprises," and "comprise."

As used herein, the term "dispersibility control agent" refers to a material added to a composition in order to control the degree of dispersibility of that composition in a fluid.

As used herein, the term "dwell time" refers to the amount of time an adhesive article has remained adhered to a substrate.

As used herein, the term "glass transition temperature" or "Tg" refers to the temperature below which the adhesive becomes brittle and fails to form an adhesive bond.

As used herein, the terms "having," "has," and "have" have the same open-ended meaning as "comprising," "comprises," and "comprise."

As used herein, the term "hold power" refers to the amount of time, in minutes, an adhesive composition can be subjected to the force of a vertical static weight before undergoing shear failure. Hold power can be determined according to PSTC Procedure 107.

As used herein, the term "humectant" refers to a hygroscopic material capable of maintaining the moisture content of a composition within a narrow range over extended periods of time despite broad fluctuations in external relative humidity.

As used herein, the term "hypoallergenic" means less likely to cause an allergic reaction.

As used herein, the terms ʌincluding,@ʌincludes,@ and ʌinclude@ have the same open-ended meaning as ʌcomprising,@ʌcomprises,@ and ʌcomprise.@

As used herein, the term "ion" refers to one or more atoms with a positive charge or a negative charge caused by gaining or losing an electron.

As used herein, the term "ionic liquid" refers to a liquid whose ion content is greater than about 5 grams per liter.

As used herein, the term "low-ion liquid" or "liquid of low-ion content" refers to a liquid that comprises less than about 5 grams per liter, or less than about 1.5 grams per liter, or less than 0.1 grams per liter of ions.

As used herein, the term "moisture mass uptake" or "MMU" refers to the amount of water, expressed as a percentage of the final wet weight of the adhesive, that an adhesive composition is capable of absorbing from its environment. Example 2 describes the procedure to determine the moisture mass uptake of an adhesive composition.

As used herein, the term "molecular weight" refers to the sum of the atomic weights of all the atoms in a molecule.

As used herein, the term "neutral pH" or "pH-neutral" refers to a material with a pH in the range of from about 6 to about 8.5, about 6.5 to about 8.25, or 7 to 8.

As used herein, the term "nominal pressure" refers to the amount of pressure, typically applied with one's hands or a comparable source that is applied to an article to adhere it to a surface.

As used herein, the term "non-crystalline" refers to a material with atoms or molecules not arranged in a regular ordered, repeating pattern.

As used herein, the term "non-skin irritant" refers to a material that does not irritate the wearer's skin. In general, non-skin irritants do not comprise components typically known to cause skin irritation, such as, for example, latex and/or acrylic. Further, materials regarded as non-skin irritants may be listed by the Food and Drug Administration on the Generally Recognized as Safe (GRAS) list As used herein, the term "physical mixture" refers to the state of a composition wherein the components are not chemically combined or integrated.

As used herein, the term "plasticizer" refers to a material added to an adhesive to lower the adhesive's glass transition temperature and increase the adhesive's flexibility and durability.

As used herein, the term "polar" refers to a material comprising any amount of a material that includes one or more polar groups.

As used herein, the term "polymer ratio" or "polymer weight ratio" refers to the weight ratio of a branched polyester to a linear polyester.

As used herein, the term "polyol" refers to a chemical compound with at least two hydroxyl functional groups.

As used herein, the term "reduction in average skin peel strength" refers to the difference in the average dry skin peel strength and the average wet skin peel strength of an adhesive composition, divided by the average dry skin peel strength, and expressed as a percentage. Skin peel strength can be determined in accordance with the procedure described in Example 5.

As used herein, the term "reduction in average standard peel strength" refers to the difference in the average dry standard peel strength and the average wet standard peel strength of an adhesive composition, divided by the average dry standard peel strength, and expressed as a percentage.

Standard peel strength can be determined according to the modified procedure in PSTC-101 as described in Example 4.

As used herein, the term "relative humidity" refers to the ratio of the amount of water vapor in the air at a specific temperature to the maximum amount that the air could hold at that temperature, expressed as a percentage.

As used herein, the term "salt" refers to a compound comprising a positive ion and a negative ion, wherein the compound retains overall charge neutrality.

As used herein, the term "skin irritants" refers to compounds and/or moieties that can cause skin irritation, such as, for example, acrylic and latex.

As used herein, the term "switchable" refers to the property of an adhesive composition that allows a significant reduction in the peel strength upon contact with low-ion liquid.

As used herein, the term "tack" or "loop tack" refers to the stickiness of an adhesive or its ability to adhere firmly to a surface. Loop tack is a specific type of tack measured in accordance with PSTC Procedure 16.

As used herein, the term "tackifier" refers to an additive added to the adhesive in order to increase the softening point and prevent cold flow.

As used herein, the term "water" refers to deionized water, tap water, and any mixture thereof.

As used herein, the term "water-dispersible" refers to the property of a substance that allows it to be dispersible in a liquid comprising a polar material, such as, for example, water.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

We claim:

1. A switchable adhesive article suitable for attachment to the skin, said article comprising: a porous backing and a pressure sensitive adhesive (PSA) applied to said porous backing, wherein said PSA comprises at least one water-dispersible amphiphilic polyester and a humectant in physical mixture with said polyester; and wherein said PSA is sufficiently switchable such that when a low-ion liquid is applied to said porous backing said liquid travels through said porous backing and into contact with said PSA to thereby reduce the average wet skin peel strength of said PSA to less than 50 percent of the average dry skin peel strength of said PSA.

2. The article according to claim 1 wherein said PSA has a pH in the range of from about 6.5 to about 8.25.

3. The article according to claim 1 wherein said PSA comprises greater than about 90 weight percent of said amphiphilic water-dispersible polyesters.

4. The article according to claim 1 wherein said PSA comprises in the range of from about 0.5 to about 10 weight percent said humectant.

5. The article according to claim 1 wherein said PSA comprises greater than 95 weight percent of said amphiphilic water-dispersible polyesters.

6. The article according to claim 1 wherein said PSA comprises in the range of from 1 to 4 weight percent of said humectant.

7. The article according to claim 1 wherein said amphiphilic water-dispersible polyester is a water-dispersible sulfonated polyester.

8. The article according to claim 1 wherein said cold flow reducing agent has a molecular weight less than about 750 grams per mole.

9. The article according to claim 7 wherein said PSA consists essentially of a blend of at least one linear water-dispersible sulfonated polyester and at least one branched water-dispersible sulfonated polyester and a humectant in physical mixture with said polyesters.

10. The article according to claim 1 wherein said article is a wound dressing, a surgical dressing, a medical tape, an athletic tape, a tab or tape used to adhere medical devices, or an adhesive device for transdermal drug delivery.

11. A method of attaching and removing a switchable adhesive article to and from skin, said method comprising:

adhering a switchable adhesive article to skin, wherein said adhesive article comprises a backing and a pressure sensitive adhesive (PSA) applied to a first side of said backing, wherein said PSA comprises at least one sulfonated water-dispersible polyester;

applying low-ion liquid to said PSA; and subsequent to step (b), removing said article from said skin, wherein the average skin peel strength of said PSA subsequent to step (b) is less than about 75 percent of the average skin peel strength of said PSA prior to step (b).

12. The method according to claim 11 wherein said PSA has a pH in the range of from about 6.5 to about 8.25.

13. The method according to claim 11 wherein said backing is sufficiently porous to allow water applied to a second side of said backing to travel through said backing and into contact with said PSA on said first side of said backing.

14. The method according to claim 11 wherein said backing is sufficiently porous to allow water applied to said second side of said backing to travel through said backing and into contact with at least about 10 percent of the area of said PSA applied to said first side of said backing.

15. The method according to claim 11 wherein said low-ion liquid is polar.

16. The method according to claim 11 wherein said low-ion liquid comprises less than about 5 grams per liter ions.

17. The method according to claim 11 wherein said low-ion liquid comprises water.

* * * * *